United States Patent
Limousin

(10) Patent No.: US 8,428,714 B2
(45) Date of Patent: Apr. 23, 2013

(54) ACTIVE IMPLANTABLE MEDICAL DEVICE WITH ATRIAL PACING FOR THE TREATMENT OF DIASTOLIC HEART FAILURE

(75) Inventor: Marcel Limousin, Paris (FR)

(73) Assignee: Sorin CRM S.A.S., Clamart (FR)

( * ) Notice: Subject to any disclaimer, the term of this patent is extended or adjusted under 35 U.S.C. 154(b) by 0 days.

(21) Appl. No.: 13/340,535

(22) Filed: Dec. 29, 2011

(65) Prior Publication Data

US 2012/0172943 A1   Jul. 5, 2012

(30) Foreign Application Priority Data

Dec. 29, 2010 (FR) ..................... 10 61335

(51) Int. Cl.
*A61N 1/00* (2006.01)
(52) U.S. Cl.
USPC .............................................. 607/5
(58) Field of Classification Search ........... 607/5
See application file for complete search history.

(56) References Cited

U.S. PATENT DOCUMENTS

| | | | |
|---|---|---|---|
| 5,304,208 A | 4/1994 | Inguaggiato et al. | |
| 6,556,866 B2 | 4/2003 | Dal Molin et al. | |
| 6,658,295 B1 * | 12/2003 | Sloman ................... | 607/28 |
| 7,966,065 B2 | 6/2011 | Limousin | |
| 2002/0151934 A1 | 10/2002 | Levine | |
| 2005/0102002 A1 | 5/2005 | Salo et al. | |
| 2007/0179541 A1 | 8/2007 | Prakash et al. | |
| 2007/0179542 A1 | 8/2007 | Prakash et al. | |
| 2009/0209875 A1 | 8/2009 | Giorgis et al. | |
| 2010/0125308 A1 | 5/2010 | Casset | |
| 2010/0125309 A1 | 5/2010 | Casset | |

FOREIGN PATENT DOCUMENTS

| | | |
|---|---|---|
| EP | 0515319 | 11/1992 |
| EP | 1108446 | 6/2001 |
| EP | 2092885 | 8/2009 |
| EP | 2189180 | 5/2010 |
| EP | 2189182 | 5/2010 |
| EP | 2206531 | 7/2010 |
| WO | WO 2005/011803 | 2/2005 |

OTHER PUBLICATIONS

Foreign Search Report (Annexe Au Rapport De Recherche Preliminaire Relatif A La Demande De Brevet Francais No. FR1061335 FA745713), Apr. 13, 2011.

* cited by examiner

*Primary Examiner* — George Manuel
(74) *Attorney, Agent, or Firm* — Orrick Herrington & Sutcliffe, LLP

(57) ABSTRACT

An active implantable medical device with atrial pacing for the treatment of diastolic heart failure. This device comprises circuits and leads for collecting right and left atrial events (16,18) and pacing the left atrium (18) and a sensor detecting myocardium contractions, preferably an endocardial acceleration sensor (20), delivering a signal representative of the myocardium contractions. Analysis of the signal allows a determination of the presence or absence of a detectable left atrial contraction distinguishable from the ventricular contraction. An interatrial delay is applied between the collection of a right atrial depolarization and the delivery of a left atrial pacing pulse. In the absence of left atrial contraction, the interatrial delay is iteratively reduced in successive cardiac cycles from an initial value to an adjustment value ensuring that a left atrial contraction appears, and then so maintained while the presence of a left atrial contraction continues.

10 Claims, 3 Drawing Sheets

ACTIVE IMPLANTABLE MEDICAL DEVICE WITH ATRIAL PACING FOR THE TREATMENT OF DIASTOLIC HEART FAILURE

The present application claims the benefit of French application Ser. No. 10/61335 entitled "Active Implantable Medical Device with Atrial Pacing for The Treatment of Diastolic Heart Failure" and filed Dec. 29, 2010, which is hereby incorporated by reference in its entirety.

FIELD RELATED APPLICATIONS

The present invention relates to "active implantable medical devices" as defined by the 20 Jun. 1990 Directive 90/385/EEC of the Council of the European Communities, more specifically to devices that continuously monitor a patient's cardiac rhythm and deliver if necessary to the patient's heart electrical pulses for stimulation, cardiac resynchronization, cardioversion and/or defibrillation, in response to a rhythm disorder detected by the device, and even more particularly to devices that address heart failure, in alternation and in addition to cardiac rhythm disorders.

BACKGROUND

It has been proposed to use stimulation of the heart chambers to control disorders of myocardial contraction observed in patients with heart failure, whether the disorders were spontaneous or induced by traditional stimulation. This therapy has often observed dramatic positive results for patients with heart failure whose condition was not improved with conventional treatments.

This therapy is designed to resynchronize the contraction of the heart chambers (atrium and ventricle, and both ventricles) in order to improve the patient by optimizing the different phases of the hemodynamics cycle, this cycle including: pre-ejection, isovolumetric contraction, systolic ejection, isovolumetric relaxation, and finally filling of the cavity.

Most of these known devices implement a technique called cardiac resynchronization therapy ("CRT") or bi-ventricular pacing ("BVP"), delivering as needed electrical pulses to ensure a joint and permanent stimulation of the left and right ventricles to resynchronize them. For this purpose a device with electrodes to stimulate both ventricles is implanted in a patient, the device applying between the respective moments of stimulation of the left and right ventricles a delay, called "interventricular delay." The interventricular delay can be adjusted to resynchronize the contraction of both ventricles with fine optimization of the patient's hemodynamic status. Such a CRT pacemaker is, for example, disclosed in EP 1108446 A1 and its counterpart U.S. Pat. No. 6,556,866 (both assigned to Sorin CRM S.A.S., of Clamart, France, previously known as ELA Medical, of Montrouge, France), which is incorporated herein by return in its entirety.

This technique of biventricular resynchronization only addresses, however, the form of heart failure known as "systolic failure." In this form of the disease, the heart muscle is unable to provide the force necessary to ensure adequate cardiac output, and the patient shows signs of dilatation, leading to a lengthening of the QRS complex, which is the expression of delayed left ventricular depolarization, resulting in desynchronization. A CRT/BVP device can then resynchronize the ventricles and make the cardiac contraction more uniform.

There is another form of heart failure, known as "diastolic failure," which is a failure with "preserved systolic function" and has no characteristic of desynchronization of the ventricles. Rather, it comes from a lack of or incomplete left ventricular filling.

A CRT/BVP therapy is of no effect in this case. However, the diastolic failure form of the disease affects nearly 40% of heart failure patients, and there is no known effective treatment to address it.

The starting point of the present invention is the recognition by the inventor that this clinical form of disease may particularly be the result of a conduction disorder in the atria (interatrial block), which delays the depolarization, and therefore the contraction, of the left atrium from the right atrium. However, as the atrio-ventricular conduction paths otherwise behave normally, the depolarization and contraction of both ventricles occurs within a reasonable time, and with no desynchronization between the ventricles. Therefore, the interatrial block introduces a poor synchronization between the contraction of the left atrium and the left ventricle: the delay of the contraction of the left atrium is such that it contracts almost simultaneously with the left ventricle, and therefore can not properly fullfil its function to finish the filling of the left ventricle.

The U.S. Patent Publication No. 2005/0102002 A1 describes a device equipped with a sensor measuring a hemodynamic parameter (intra-ventricular pressure sensor, pulmonary venous flow sensor, flow sensor through the mitral valve, acoustic sensor, and accelerometer) the signal of which is used to calculate a representative index of the diastolic function of the patient. The stimulation parameters are modified as necessary to maximize the performance index, for example, by appropriate selection of the stimulation sites and/or control of the atrio-ventricular delay.

The U.S. Patent Publication No. 2007/0179542 A1 describes another device of the same type, including a sensor delivering an LV acceleration signal representative of the contraction of the left ventricle. The device also comprises means for varying the atrioventricular (AV) and interatrial (AA) delays based on various parameters, including the LV acceleration signal of the left ventricle, to try to improve the patient's cardiac function. This document provides in particular to adjust iteratively the AV delay based on the LV acceleration signal measured, until an optimal sequencing value between the contractions of the atrium and those of the ventricle is found.

Other techniques have been proposed for treating diastolic heart failure, such as effecting a premature stimulation of the left atrium either by "overdrive", a technique of stimulation of the left atrium at a frequency slightly higher than the frequency of a spontaneous sinus rhythm (i.e., the rhythm of the right atrium), or triggering the stimulation of the left atrium from the detection of the depolarization of the right atrium.

Both methods are purely electric (i.e., they are based on the detection of the depolarization signals), and their effectiveness can only be validated by a hemodynamic analysis, for example, by an echocardiographic examination. In addition, they provide no adaptation for exercise in case of a change of patient activity, or in case of possible changes in the conduction of the cardiac tissue over time.

OBJECT AND SUMMARY

It is, therefore, an object of the present invention to propose a new apparatus, method and technique for treatment of diastolic heart failure by interatrial block.

It is another object of the present invention to provide such a technique that avoids the measurement and calculation of an index of diastolic performance, so as to ensure recovery of the diastolic function in a manner that is both simple (in terms of computing resources) and very reactive (efficiency obtained cycle by cycle).

The present invention therefore is broadly directed to operate exclusively by atrial stimulation (bi-atrial stimulation), with a coordinated stimulation of the two atria to restore a satisfactory sequence of contraction of the left atrium from the ventricle, so that the atrium can properly fulfil its function of completing the left ventricular filling.

One embodiment of the invention is directed to an active implantable medical device having a contraction a sensor delivering a signal representative of mechanical movements produced by contractions of the heart associated with a cardiac cycle. Such a contraction sensor may be, for example, a pressure sensor or, more preferably, an endocardial acceleration (EA) sensor incorporated into an implanted lead, as described, for example, in EP 0515319 A1 and its counterpart U.S. Pat. No. 5,304,208 (both assigned to Sorin Biomedica Cardio SpA) which disclosures are incorporated by reference herein in their entirety. This document teaches a method to collect an EA signal using a endocardial lead equipped with a distal stimulation electrode implanted at the apex of the ventricle and integrating a microaccelerometer coupled to the heart muscle for measuring endocardial acceleration. Such a sensor provides a functional signal (the EA signal) representative of the mechanics of the heart, not a signal from the electrical propagation of the depolarization wave as delivered from the detection electrodes of the lead.

It should be understood, however, that although the present description mainly refers to the analysis of an EA signal delivered by a sensor placed on an endocardial lead, the invention is also applicable to an analysis conducted from an EA signal delivered by other types of implanted sensors, such as a cardiac wall motion sensor, an epicardial sensor or an accelerometer placed in the case of an implant, as long as it collects an endocardial acceleration (EA) signal representative of the contractions of the atrium.

Several clinical studies have shown that endocardial acceleration is a parameter that very accurately and in real time reflects, both in the case of normal operation and in the case of a deficient functioning, the mechanical phenomena related to the movements of the heart chambers—including the atria, in the case of the present invention.

In particular, the atrial contraction (systole) is expressed by the presence in the EA signal of a specific component, called EA4, which can be distinguished from the contraction of the ventricles. Moreover, the largest cardiac mass being that of the left heart cavities, the EA4 component of the EA signal essentially corresponds to the activity of the left atrium.

One effect of atrial systole is to complete the power of the ventricular muscle and to cause the start of the contraction of the left ventricle. But in the case of a patient with diastolic heart failure following an interatrial block, the delay of the contraction of the left atrium is such that the EA4 component associated with the atrial contraction (mainly, with the contraction of the left atrium) is embedded in the ventricular contraction, and cannot be detected and isolated in the collected EA signal.

To find an effective left atrial systole, discernible from the ventricular systole on the EA4 signal, one embodiment of the invention stimulates the left atrium with an atrial delay that is gradually reduced until an atrial contraction with a prematurity sufficient to distinguish it from the contraction of the left ventricle is detected. This configuration corresponds to a correct sequencing of the contraction of both left cavities, and thus to a compliant or adequate diastolic function.

One aspect of the invention includes, in a known manner and as disclosed by US Patent Publication No. 2007/0179542 A1 cited above: an active implantable medical device comprising means for collecting right atrial depolarizations, means for collecting left atrial depolarizations, and means for delivering left atrial pacing pulses; a contraction sensor for delivering a signal representative of the contraction movements produced by contractions of the myocardium associated with a cardiac cycle; means for analyzing the contraction signal, for determining an occurrence of a left atrial contraction, temporally distinguishable from a ventricular contraction of the same cardiac cycle; and means for determining and applying to the means for delivering left atrial pacing pulses an interatrial delay between the collection of a right atrial depolarization and the delivering of a left atrial pacing pulse, this interatrial delay being modifiable according to the contraction signal.

Preferably, the device further comprises means for restoring the patient's diastolic function, comprising: a contraction sensor responsive to the movements of the myocardium and having an output signal representative of the movements produced by cyclical contractions of the myocardium; means for analyzing said signal and determining an occurrence of a left atrial contraction, temporally distinguishable from a ventricular contraction of the same cardiac cycle; means for determining an interatrial delay between the collection of a right atrial depolarization and the delivery of a left atrial pacing pulse and implementing said interatrial delay in said means for delivering a left atrial pacing pulse; and means for, in the absence of a determined left atrial contraction, iteratively reducing the interatrial delay during successive cardiac cycles, from an initial value to an adjustment value that ensures an occurrence of a left atrial contraction revealed by the analysis means, the interatrial delay then being maintained at said adjustment value as long as the occurrence of a left atrial contraction is determined by the analysis means.

In a preferred embodiment, the contraction sensor is disposed on an atrial implantable lead, in one of the atria, preferably the right atrium. More preferably, the contraction sensor is an endocardial acceleration sensor, and the analysis means comprises means for recognizing and isolating in the signal delivered by the contraction sensor an EA4 component corresponding to the fourth peak of endocardial acceleration associated with atrial activity. The presence of the EA4 component determines the occurrence of a left atrial contraction temporally distinguishable from the ventricular contraction of the same cardiac cycle;

In one embodiment, the contraction sensor may be a left endocardial cardiac pressure sensor.

In one embodiment, the device further comprises means for measuring, on a spontaneous rhythm in the absence of atrial pacing, a time interval between the collection of a right atrial depolarization and that of a consecutive left atrial depolarization, and for determining an initial value of the interatrial delay from the interval thus measured.

In one embodiment, the device further comprises means for, in case the adjustment value is lowered below a given minimum value with no detection by the analysis means of the presence of a left atrial contraction, controlling the delivery of left atrial pacing pulses with a coupling interval that is iteratively reduced to a value ensuring the appearance of said left atrial contraction, the coupling interval then being maintained at this value as long as a left atrial contraction is determined by the analysis means.

In another embodiment, the device is essentially free of means for delivering ventricular pacing pulses, and of means for collecting ventricular depolarizations. It should be understood by a person of ordinary skill in the art that to implement the present invention, there is no need for delivery of ventricular pacing and/or detection of ventricular depolarizations. The latter can certainly exist, for example, in the case of a multisite pacemaker providing, in addition to stimulation of the atria, the stimulation of the right ventricle or even that of the two ventricles (four chamber pacemaker). But these ventricular pacing and detection functions are not involved in the treatment of diastolic heart failure according to the present invention, which aims to overcome a pre-existing conduction disorder between the atria, that is to say an inter-atrial block, resulting in undue delay (or even absence) of conduction between the right atrium and the left atrium.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which.

DETAILED DESCRIPTION

With reference to FIGS. 1-4, a preferred embodiment of a device according to the present invention will now be described.

As regards its software aspects, the present invention can be implemented by an appropriate programming of the control software of a known active implantable medical device, for example, a cardiac pacemaker or a defibrillator/cardioverter, already including circuits and software for collecting a signal provided by endocardial leads and/or one or more implanted sensors. In this regard, the present invention may particularly be applied to implantable devices such as those of the Ovatio and Paradym device families produced and marketed by Sorin CRM, Clamart France, formerly known as ELA Medical, Montrouge, France. These devices include programmable microprocessor circuitry to receive, format, and process electrical signals collected (detected) by electrodes implanted and deliver stimulation pulses to these electrodes. It is possible to transmit by telemetry software instructions that will be stored in a memory of the implantable devices and executed to implement the functions of the invention that will be described herein. The adaptation of these known devices to implement the functions and features of the present invention is believed to be within the abilities of a person of ordinary skill in the art, and therefore will not be described in detail.

Figure 1:
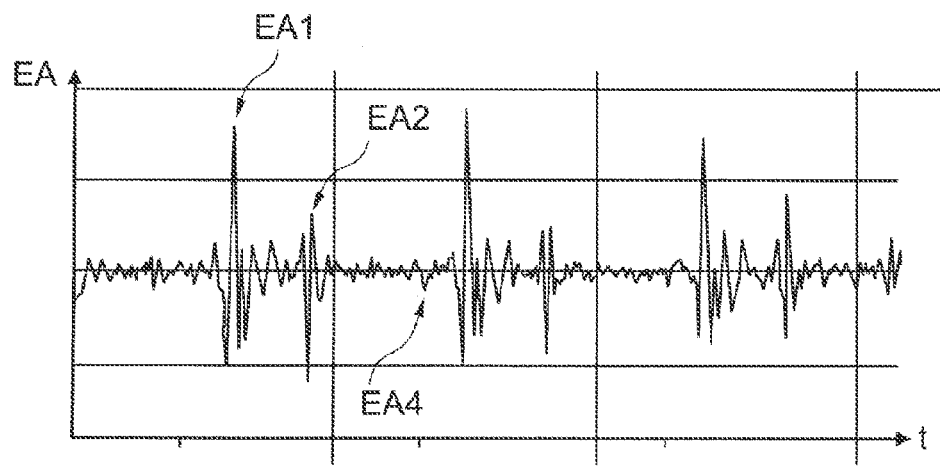
FIG. 1 illustrates a representative endocardial acceleration EA signal collected during three consecutive cardiac cycles.

As shown in FIG. 1, the endocardial acceleration signal EA collected during a given cardiac cycle (the "signal EA") forms two main components (hereinafter "EA components"), corresponding to the two major heart noises (sounds S1 and S2 of the phonocardiogram) it is possible to recognize in each cardiac cycle:

The first endocardial acceleration component ("EA1 component"), the amplitude variations of which are closely linked to the changes in pressure in the ventricle (the maximum peak to peak amplitude, called "PEA1" of this EA1 component is specifically correlated with the maximum positive pressure variation dP/dt in the left ventricle) and can therefore be a parameter representative of the myocardial contractility, which in turn is related to the activity level of the sympathetic system;

The second component of endocardial acceleration ("EA2 component") which occurs during the phase of isovolumetric ventricular relaxation and of abrupt deceleration of the blood mass in motion in the aorta. This second component is mainly produced by closure of the aortic and pulmonary valves, and corresponds to the S2 sound of the phonocardiogram.

The EA signal also contains two other components, of a much lower amplitude, called EA3 and EA4, corresponding to the S3 and S4 sounds of the phonocardiogram.

The present invention relates more particularly to the EA4 component, which is directly related to the presence of an atrial contraction.

As shown in FIG. 1, the EA4 component is located immediately before the EA1 component. For this reason, it is sometimes referred to as "EA0" component by physicians, to the extent that, from an electrical point of view, the atrial contraction precedes the ventricular contraction, but from the blood flow pumped by the heart muscle point of view, the contraction of the atrium (corresponding to the EA4 component) completes the filling of the ventricle at the end of the diastole (EA2 component) and is therefore, in terms of cardiac hemodynamics, after the latter—hence the name "EA4".

The presence of this EA4 component can be determined through a technical analysis of the EA signal as described for example in EP 2189180 A1 (and its counterpart US Patent Publication No. 2010/0125308) or EP2189182 A1 (and its counterpart US Patent Publication No. 2010/0125309) (all assigned to Sorin CRM S.A.S, Clamart, previously known as ELA Medical, Montrouge), allowing in particular to search for and confirm the presence of an EA4 component, and precisely define the moments of start and end of it in the cardiac cycle.

Figure 2:
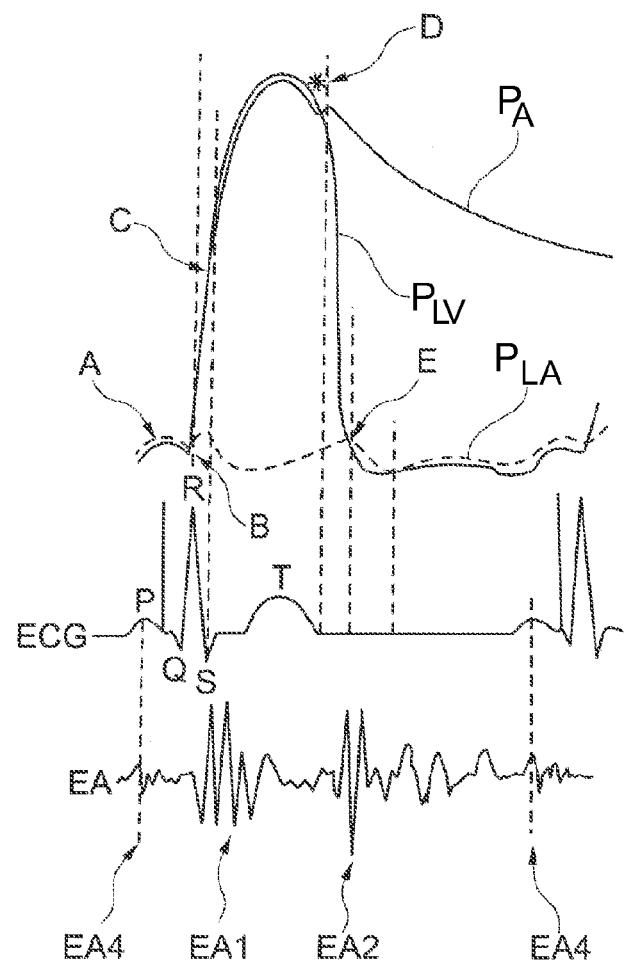
FIG. 2 is a series of three timing diagrams illustrating various signals characterizing the cardiac activity during a given cycle.

Referring to FIG. 2, the different signals characterizing the activity of the heart during a cardiac cycle are shown, with: the profile of intracardiac pressures (the top plot), a plot of surface electrocardiogram (ECG), and the changes in the endocardial acceleration (EA) signal (also referred to herein as signal EA).

On the profile of intracardiac pressures, the following characteristics show the changes in aortic pressure $P_A$, left ventricle pressure $P_{LV}$ and left atrium pressure $P_{LA}$. The points labeled A to E correspond to the different following phases: A, contraction of the left atrium, B, closure of the mitral valve, C, opening of the aortic valve, D, closure of the aortic valve, and E, opening of the mitral valve.

The ECG signal comprises in succession: the P wave corresponding to the depolarization of the atrium, the QRS complex corresponding to the ventricular depolarization and the T wave of ventricular repolarization.

The endocardial acceleration signal EA, meanwhile, can be broken down as follows: the EA4 component corresponds to the contraction of the atrium (P wave), and is followed by the EA1 component, which begins after the QRS and is caused by a combination of the closure of the atrioventricular valves, of the opening of the semilunar valves and of the contraction of the left ventricle. The EA2 component which follows accompanies the end of the ventricular systole and is generated by the closure of the semilunar valves.

The signal EA is thus a functional signal representative of the mechanics of the heart, distinct from the electrical signal of depolarization collected after onset of a spontaneous or stimulus event—in this case, an atrial, right or left, event.

Figure 3:
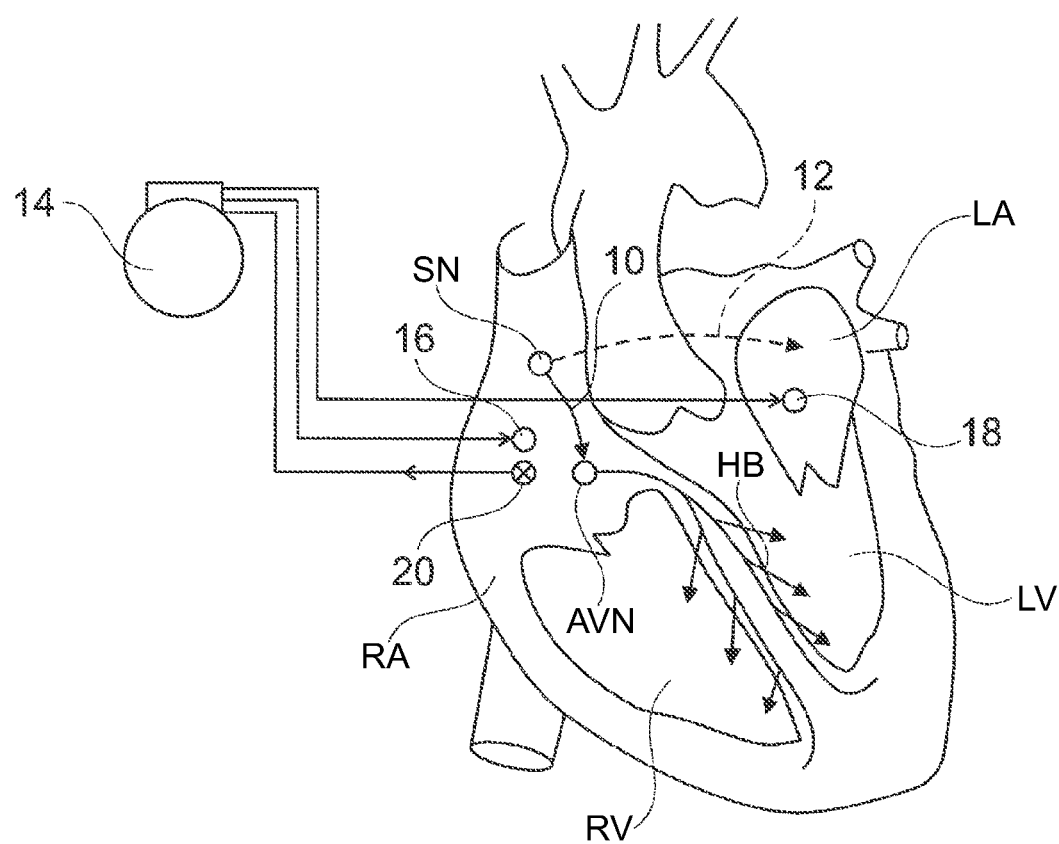
FIG. 3 is a schematic drawing showing the position of the different sites involved in the cyclical, spontaneous or stimulated electrical activity of the heart.

FIG. 3 illustrates a diagram of the heart with its four chambers: right atrium RA, right ventricle RV, left atrium LA and left ventricle LV.

The coordinated contraction of the different cavities is originated at the sinus node SN, then the depolarization wave is conducted at the atrioventricular node AVN (conduction represented by the arrow 10), then from this node to the Bundle of His (HB), and finally, the tissues of right and left ventricles RV and LV, resulting in their contraction.

Moreover, the wave of depolarization originated by the sinus node SN causes contraction of the right atrium RA and, after interatrial conduction (conduction represented by arrow 12) to the left atrium LA, causing its contraction.

In the case of a patient with diastolic heart failure, atrioventricular conduction (arrow 10, from the sinus node SN to the atrioventricular node AVN) is preserved, as well as the conduction pathways to ensure a synchronous contraction of the right and left ventricles RV and LV.

However, the interatrial conduction (arrow 12) can be altered, causing a delay of depolarization and therefore contraction of the left atrium LA compared to the ventricles. This leads to a bad sequence of contraction of the left atrium LA compared to that of the left ventricle LV, with a more or less simultaneous contraction of these two cavities. As a result, the left atrium LA can no longer properly fulfil its function, which is to finish filling the left ventricle LV.

The present invention provides a technique for the diagnosis of and therapy for this disease, preferably using a pacemaker acting only on the two atria.

This pacemaker includes a generator 40 inside a case 14 connected to an electrode 16 for stimulation/collection of depolarizations in the right atrium RA, and an electrode 18 for stimulation/collection of depolarizations in the left atrium LA. The electrode 18 may be preferably positioned in the coronary sinus, or in the atrial septum, or directly into the left atrium after an atrial septal puncture.

Preferably, the lead placed at the right atrium is also equipped with a contraction sensor 20 for delivering a functional signal representative of mechanical contractions (and not depolarizations) of the heart chambers, more preferably an endocardial acceleration signal EA of the type described above with reference to FIGS. 1 and 2. The electrode 16 and the contraction sensor 20 are preferably arranged on a conventional endocardial lead, implanted at the right atrium via the venous system. It should be understood however, that electrode 16 and any contraction sensor 20 could be provided using separate leads when deemed suitable.

The contraction sensor 20 is sensitive to the movement of the heart walls, and generates an output signal, preferably of the heart wall acceleration, having an amplitude mainly corresponding to the activity of the left atrium and of the left ventricle, given that the largest cardiac mass is the left heart cavities (notwithstanding even that the sensor may be implanted on the right heart side).

In the example shown, the contraction sensor 20 is located in the atria, on an atrial lead, because the implantable device is an "atrial dual chamber" device, devoid of any ventricular sensing/pacing means. It is in addition disposed on the right atrial lead because it is easier to integrate a contraction sensor in the latter (endocardial lead) than in the case of a left atrial lead (which typically is very thin lead, introduced in the coronary network or through the interatrial septum). But other locations for the contraction sensor are possible, for example, on a ventricular lead in the case of a "triple chamber" pacemaker, as long as the collected contraction signal allows characterizing the atrial contraction, i.e., the EA4 component is sufficiently discernable on the collected signal EA.

Figure 4:
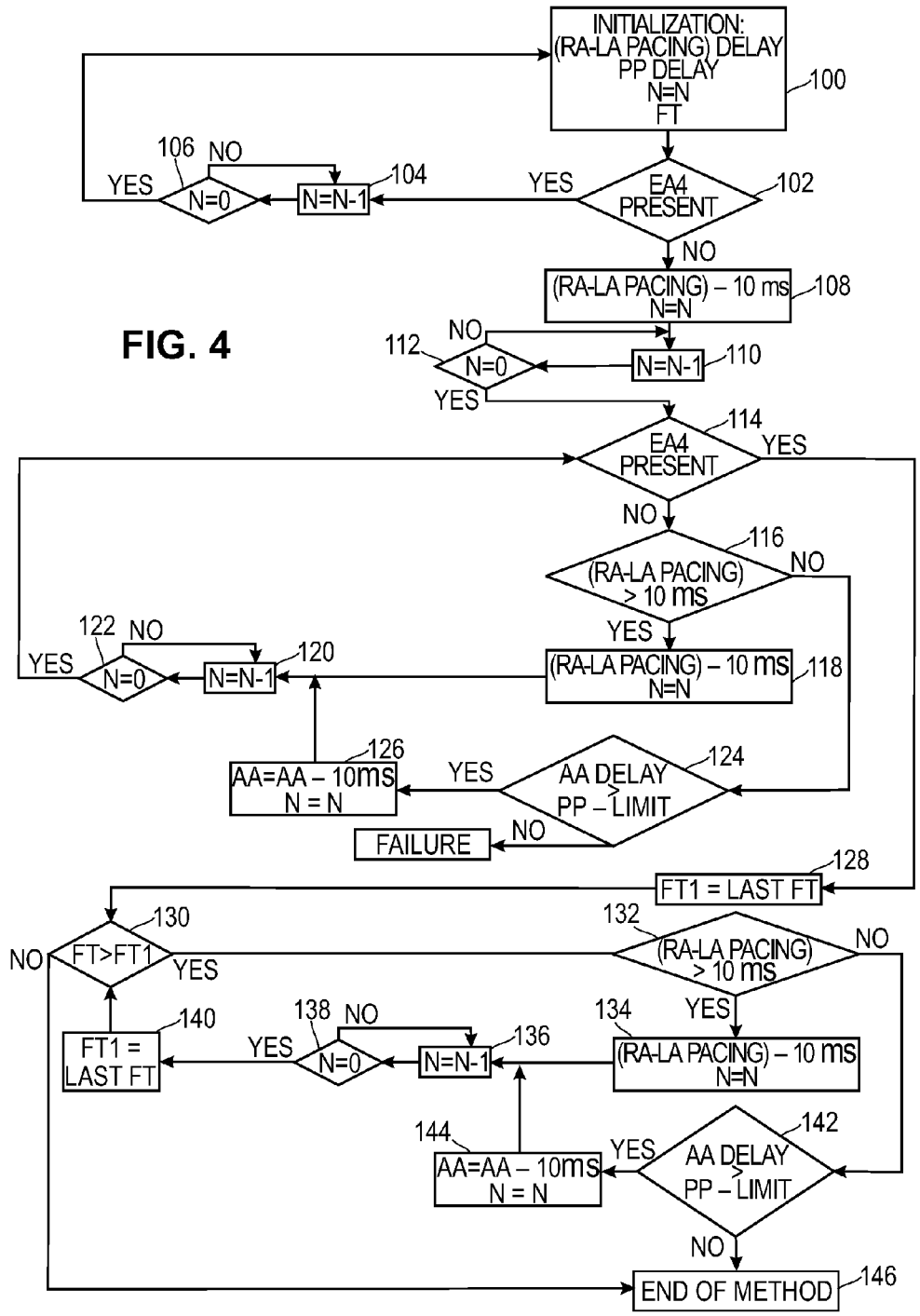
FIG. 4 is a flowchart of a process implemented by a preferred embodiment of the present invention.

FIG. 4 is a detailed flow chart showing a method for processing the signals collected by electrodes 16, 18 and contraction sensor 20, in accordance with a preferred embodiment of the invention.

The first phase (step 100) is to make an initial analysis of a spontaneous rhythm with: a measure of the interatrial delay (referred to as "RA-LA pacing") between the spontaneous depolarizations of the right atrium and the left atrium, a measure of the PP atrial coupling interval (the time between two atrial depolarizations in the same cavity, representing the duration of one cardiac cycle having a spontaneous rhythm), and measure of the filling time FT. The cycle counter is also initialized to a predetermined value N. The value N may be a predetermined number of cardiac cycles, for example, between 5 and 10 consecutive sinus rhythm cycles.

The contraction sensor 20 in this embodiment is an EA sensor which produces a signal EA, which is then analyzed by the software routine to determine whether an EA4 component is present (step 102). The absence of a detectable EA4 component means that the contraction of the left atrium LA is masked by the contraction of the left ventricle LV, and therefore the atrium contraction is delayed and does not fullfil its function of completing the filling the left ventricle at the end of its diastole. A detectable EA4 component means that the contraction of the left atrium LA occurs before the contraction of the left ventricle LV at the end of the diastole, with a correct sequencing allowing the atrial contraction to complete the ventricular filling before the latter begins to contract.

If the EA4 component is present, there is no need to take special action, and the process awaits the end of the N cycles (steps 104, 106) before repeating the previous phase of initialization of step 100.

If in step 102 the determined absence of an EA4 component is confirmed after detection of the spontaneous contraction of the right atrium RA, stimulation is delivered to the left atrium LA, with application of a delay (referred to as "RA-LA pacing") corresponding to the spontaneous interatrial delay measured in step 100, reduced by a fixed step, for example, a step of 10 ms (step 108). The cycle counter is also reset to N.

On completion of N cycles (steps 110, 112), the determined presence of an EA4 component is tested again (step 114).

If the EA4 component is determined present, the stimulation is maintained with the same delay (steps 128-146, described below).

If the EA4 component is determined absent, and if the period of atrial pacing RA-LA pacing is not at its minimum (step 116), then this delay is further reduced by one step, and the stimulation is delivered under these conditions for N cycles (steps 118, 120 and 122 which are counterparts of steps 108, 110 and 112 above).

If, in step 116, (i) the period of atrial pacing at the selected minimum value (10 ms or less), (ii) the EA4 component is still determined absent, and (iii) the atrial pacing interval AA is greater than the coupling interval PP in spontaneous rhythm, to a limit value, then a left atrial pacing is delivered with an AA interval equal to the duration of the sinus (i.e., a spontaneous) cycle length decreased by 10 ms (step 126), and so on for N cycles (steps 120, 122) until the determined appearance of an EA4 component (step 114 above).

Advantageously, but optionally, once the EA4 component has been detected in the test in step 114, the process performs an additional optimization by comparative measurement of the filling time FT.

These aspects are particularly described in EP 2206531 A1 and its counterpart U.S. Pat. No. 7,966,065 (both assigned to Sorin CRM S.A.S., Clamart, previously known as ELA Medical, Montrouge), which describes the method to analyze a number of hemodynamic parameters, including the filling time FT, to optimize the adjustment of the stimulation parameters, and which are incorporated herein by reference. The filling time FT is the time interval between the closure of the aortic valve and the closure of the mitral valve and is usually expressed in relative terms, as a percentage of the full length of a cardiac cycle (RR duration), with an ideal value, typically FT>40%.

The moments of the different hemodynamic phases of the same cardiac cycle, allowing in particular to determine the filling time FT, can be determined by a particular technique as described in EP 2092885 A1 and its counterpart US Patent Publication No. 2009/0209875 both assigned to Sorin CRM S.A.S., Clamart, previously known as ELA Medical, Montrouge), where the different temporal markers of the characteristic instants of the cardiac cycle are determined by analyzing a signal EA. Data provided by the EA signal indeed reflects very precisely and in real time, as explained above, the phenomena contributing to the mechanical function of the heart and thus make it possible, after filtering and analysis, to provide temporal markers of the systole and other hemodynamic performance indexes of the myocardium. These parameters can be determined in real time, beat by beat, which optimizes the therapy immediately applied to the patient.

In accordance with the present invention, a comparative measurement is performed between the filling time in spontaneous rhythm (FT parameter measured at the initial stage 100) and that measured after the determined reappearance of the EA4 component following controlled stimulation.

Thus, after measuring the value FT1 of the last filling time (step 128), it is examined whether the filling time increased from the initial value measured in step 100, in spontaneous rhythm (step 130):

If the filling time increased:
  if the delay of atrial pacing LA-RA pacing is greater than its selected minimum, 10 ms (step 132), then this delay is reduced (step 134) and stimulation is continued on these basis for N cycles (steps 136, 138 and 140), until the test in step 130 is performed again; or
  if the stimulation is in atrial "overdrive" (step 142, identical to step 124), then the pacing interval is decreased by 10 ms (step 144, identical to step 126), and as before, the stimulation is continued on these parameters on N cycles (steps 136, 138 and 140); then
If after this reducing the filling time increases (test again in step 130), then reducing the delay of atrial stimulation is continued, until a maximum filling time (repetition of steps 134 to 140); otherwise, the delays are reprogrammed to the previous value (end of the process, step 146).

One skilled in the art will appreciate that the present invention may be practiced by other than the embodiments described herein, which are presented for purposes of illustration and not of limitation.

The invention claimed is:

1. An active implantable medical device such as a cardiac prosthesis for pacing, resynchronization and/or defibrillation, comprising:
   Means (16) for collecting right atrial depolarizations;
   Means (18) for collecting left atrial depolarizations, and
   Means (18) for delivering left atrial pacing pulses,
   A contraction sensor (20), having a signal representative of movement produced by contractions of a myocardium;
   Means for analyzing said signal and determining therein an occurrence of a left atrial contraction, temporally distinguishable from a ventricular contraction for the same cardiac cycle;
   Means for identifying and applying to the means for delivering left atrial pacing pulses an interatrial delay between the collection of a right atrial depolarization and the delivery of a left atrial pacing pulse,
Wherein the means for identifying and applying further comprises:
   Means for determining an absence of a determined left atrial contraction in said signal, and for iteratively reducing the interatrial delay during successive cardiac cycles from an initial value to an adjustment value corresponding to the means for analyzing determining an occurrence of a left atrial contraction and for maintaining the interatrial delay at said adjustment value as long as the means for analyzing continues to determine in said signal a left atrial contraction so as to restore a diastolic function of a patient.

2. The device of claim 1, wherein the contraction sensor is placed on a lead implantable in one of a left atrium and right atrium of a patient.

3. The device of claim 1, wherein the contraction sensor is placed on a lead implantable in the right atrium.

4. The device of claim 1, wherein the contraction sensor further comprises an endocardial acceleration sensor.

5. The device of claim 4, wherein the analysis means comprises means for recognizing and isolating in said signal an EA4 component corresponding to a fourth peak of endocardial acceleration associated with the atrial activity, wherein said recognized isolated EA4 component corresponds to an occurrence of a left atrial contraction temporally distinguishable from the ventricular contraction of the same cardiac cycle.

6. The device of claim 1, wherein the contraction sensor further comprises a left endocardial cardiac pressure sensor.

7. The device of claim 1, further comprising means for measuring, during a spontaneous rhythm in the absence of atrial pacing, a temporal interval between the collection of a right atrial depolarization and the collection of a consecutive left atrial depolarization and determining said initial value of interatrial delay from said measured interval.

8. The device of claim 1, further comprising means for, in case the adjustment value is lowered below a selected minimum value without the means for analyzing determining an occurrence of a left atrial contraction, controlling the delivery of stimulation pulses with a left atrial coupling interval iteratively reduced to a value ensuring a determination of said left atrial contraction, the coupling interval the being maintained at said value as long as the means for analysis determines a left atrial contraction.

9. The device of claim 1 wherein the device is essentially free of means for delivering ventricular pacing pulses.

10. The device of claim 1 wherein the device is essentially free of means for collecting ventricular depolarizations.

* * * * *